(12) United States Patent
Caroli et al.

(10) Patent No.: US 10,371,644 B2
(45) Date of Patent: Aug. 6, 2019

(54) APPARATUS AND METHOD FOR OPTICAL INSPECTION OF OBJECTS, IN PARTICULAR METAL LIDS

(71) Applicant: SACMI COOPERATIVA MECCANICI IMOLA SOCIETA' COOPERATIVA, Imola (IT)

(72) Inventors: Sanzio Caroli, Castel San Pietro Terme (IT); Massimo Balducci, Imola (IT)

(73) Assignee: SACMI COOPERATIVA MECCANICI IMOLA SOCIETA' COOPERATIVA, Imola (IT)

( * ) Notice: Subject to any disclaimer, the term of this patent is extended or adjusted under 35 U.S.C. 154(b) by 0 days.

(21) Appl. No.: 15/562,480

(22) PCT Filed: Apr. 13, 2016

(86) PCT No.: PCT/IB2016/052085
§ 371 (c)(1),
(2) Date: Sep. 28, 2017

(87) PCT Pub. No.: WO2016/166668
PCT Pub. Date: Oct. 20, 2016

(65) Prior Publication Data
US 2018/0095044 A1 Apr. 5, 2018

(30) Foreign Application Priority Data
Apr. 14, 2015 (IT) .............................. BO2015A0180

(51) Int. Cl.
*G01N 21/88* (2006.01)
*G01N 21/90* (2006.01)
(Continued)

(52) U.S. Cl.
CPC ....... *G01N 21/8806* (2013.01); *G01N 21/909* (2013.01); *G01N 21/95684* (2013.01);
(Continued)

(58) Field of Classification Search
CPC ........ G01N 21/00; G01N 21/84; G01N 21/88; G01N 21/90; G01N 21/956;
(Continued)

(56) References Cited

U.S. PATENT DOCUMENTS 5,039,868 A 8/1991 Kobayashi et al.
5,365,084 A 11/1994 Cochran et al.
(Continued)

FOREIGN PATENT DOCUMENTS

EP 729572 A1 9/1996
JP 11295047 A 10/1999
(Continued)

*Primary Examiner* — Jamil Ahmed
(74) *Attorney, Agent, or Firm* — Pearne & Gordon LLP

(57) ABSTRACT

An apparatus (1) for optical inspection of objects (2), in particular metal lids, comprises: a camera (6) oriented according to a vertical viewing axis (7) to see the object (2) to be inspected positioned in an inspection station (4) and to capture an image of the object (2); a first illuminator (10) irradiating grazing light at a first frequency a second illuminator (11) irradiating top-down light at a second frequency different from the first frequency; a third illuminator (12) irradiating diffused light at a third frequency different from the first and second frequencies; a processor connected to the camera (6) for processing the captured image and deriving a first, a second and a third filtered image corresponding to the illumination contributions of the first, second and third illuminators (10, 11, 12), respectively and separately. The third illuminator (12) is mounted on a three-dimensional surface around the inspection station (4) and around an optical path defined by the camera (6), so that the emitted light rays are inclined at a plurality of different inclination angles to subject the object (2) in the inspection station (4) to diffused light at the third frequency.

18 Claims, 3 Drawing Sheets

(51) Int. Cl.
  *G01N 21/956* (2006.01)
  *G01N 21/84* (2006.01)
(52) U.S. Cl.
  CPC .................. *G01N 2021/845* (2013.01); *G01N 2021/8845* (2013.01); *G01N 2021/8887* (2013.01)
(58) Field of Classification Search
  CPC ............. G01N 21/8806; G01N 21/909; G01N 21/95684; G01N 2021/845; G01N 2021/8845; G01N 2021/8887; H04N 7/18
  See application file for complete search history.

(56) References Cited

U.S. PATENT DOCUMENTS

| | | |
|---|---|---|
| 8,792,094 B2 | 7/2014 | Balducci |
| 9,448,115 B2 | 9/2016 | Sones et al. |
| 2008/0212318 A1 | 9/2008 | Wang |
| 2011/0018999 A1 | 1/2011 | Joly et al. |
| 2012/0268733 A1* | 10/2012 | Balducci ............ G01N 21/8806 356/237.1 |
| 2013/0002852 A1* | 1/2013 | Bertin ............ G01N 21/95607 348/92 |

FOREIGN PATENT DOCUMENTS

| | | |
|---|---|---|
| JP | 2007024510 A | 2/2007 |
| WO | 9106846 A1 | 5/1991 |
| WO | 2011055397 A1 | 5/2011 |

\* cited by examiner

APPARATUS AND METHOD FOR OPTICAL INSPECTION OF OBJECTS, IN PARTICULAR METAL LIDS

TECHNICAL FIELD

This invention relates to an apparatus and a method for optical inspection of objects, in particular metal lids.

The invention addresses the sector of systems for optical inspection of objects, in particular for detecting defects in metal objects such as, for example, lids of jars or tins.

The invention is thus intended for quality control of objects produced in series, for example in a continuous cycle production line.

BACKGROUND ART

Typical defects of metal lids are, for example, scratches or dents.

Examples of apparatuses for optical inspection of objects are described in patent documents EP729572B1, JP2007-024510, JP11295047A and US2008/212318.

In these solutions, the object to be inspected is illuminated in successive stages, in temporal sequence. Those solutions also involve illuminating the object with light at different frequencies to facilitate inspection of objects of different colours.

Such systems are complex, however, and have the disadvantage of requiring very long times to inspect the objects. This has a penalizing effect especially if the inspection apparatus is used in the context of a high-capacity production line. Moreover, these solutions cannot effectively distinguish between different types of defects, in particular those typical of metal lids.

Other examples of apparatuses for optical inspection of objects are described in patent documents US2008212318A1, JP2011-295047 and WO2011055397A1 (the latter in the name of the same Applicant as this invention).

In these solutions, the object to be inspected is illuminated by illuminating elements having different optical paths and irradiating light at different frequencies. This allows capturing an object in a single image containing illumination contributions of different kinds (for example, grazing light i.e. grazing light or light from above i.e. top-down light), with the possibility of separating these illumination contributions in a subsequent step of processing the image.

These solutions therefore have the advantage of guaranteeing a relatively high speed of inspection.

These solutions, too, however, are limited in their ability to reliably and effectively identify the type of defects detected, especially those typical of metal lids.

DISCLOSURE OF THE INVENTION

This invention has for an aim to provide an apparatus and a method which overcome the above mentioned disadvantages of the prior art.

More specifically, this disclosure has for an aim to provide a rapid and reliable apparatus and method for optical inspection of objects, in particular metal lids.

A further aim of this disclosure is to provide an apparatus and a method for optical inspection of objects, in particular metal lids, and which are particularly effective in identifying the defects of the metal lids.

A further aim of the disclosure is to provide an apparatus for optical inspection of objects, in particular metal lids, which is particularly simple to construct and inexpensive.

These aims are fully achieved by the apparatus and method for optical inspection of objects according to the invention as characterized in the appended claims.

More specifically, the optical inspection apparatus according to this description is designed to inspect objects (particularly, but not exclusively, metal lids) fed individually and in succession to an inspection station.

In the inspection station, the object is positioned on a supporting surface lying in a reference plane.

Preferably, the objects are moved into the inspection station by a conveyor. Preferably, the supporting surface is defined by the conveyor. Preferably, the conveyor is also configured to move the objects in a movement plane which coincides with the reference plane.

The apparatus comprises a camera designed to capture images of the objects.

The camera is mounted above the inspection station.

Further, the camera is oriented according to a vertical viewing axis to see the object to be inspected positioned in the inspection station. The expression "vertical" referred to the viewing axis is used to mean an arbitrary orientation. Preferably, the viewing axis is perpendicular to the reference plane, that is, to the movement plane.

The inspection apparatus comprises a first illuminator configured to emit rays of light at a first frequency. The expression "first frequency" is used to mean a frequency value of the light or a frequency band, that is, a frequency interval of the light.

The rays emitted by the first illuminator are inclined at a first inclination angle to the viewing axis.

Preferably, the first inclination angle is such as to subject the object (positioned in the inspection station) to grazing (in other words, grazing) light at the first frequency. Thus, for example, the first inclination angle is an angle (relative to the viewing axis) included in the interval [70; 90] sexagesimal degrees; said angle is a grazing light angle. The inspection apparatus comprises a second illuminator configured to emit rays of light at a second frequency, different from the first frequency.

The rays emitted by the second illuminator are inclined at a second inclination angle to the viewing axis. The second inclination angle is smaller than the first inclination angle. Preferably, the second inclination angle is such as to subject the object (positioned in the inspection station) to top-down light (in other words, light from above) at the second frequency. Thus, for example, the second inclination angle is an angle (relative to the viewing axis) included in the interval [0; 30] sexagesimal degrees; said angle is a top-down light angle.

The inspection apparatus also comprises a third illuminator configured to emit rays of light at a third frequency, different from the first and second frequencies. The expressions "second frequency" and "third frequency" are used with the same meaning as "first frequency" explained above. For example, the first frequency is in the red spectrum, the second in the blue spectrum and the third in the green spectrum. This example is not intended as limiting and therefore, the first, second and third frequencies may be chosen arbitrarily, provided they are sufficiently distant from each other (for example, in terms of band centre) to allow uncoupling the illumination contributions of the first, second and third illuminators in a step of processing or filtering.

This filtering, for example, is performed by a processor and is a digital filtering of the captured image data.

In another example, the filtering might by optical performed during capturing. For example, optical filtering occurs by selectively attenuating one or more wavelength intervals in such a way as to allow only the required wavelengths to pass through the filter.

The rays emitted by the third illuminator are inclined at a plurality of different inclination angles to the viewing axis.

For this purpose, the third illuminator is preferably positioned on a three-dimensional surface around the inspection station and around an optical path defined by the camera.

More specifically, the third illuminator is configured to subject the object (positioned in the inspection station) to diffused light at the third frequency.

The plurality of inclination angles (of the rays emitted by the third illuminator) corresponds to a plurality of angles (to the viewing axis); for examples, the angles of said plurality of angles are included in the interval [0; 90] sexagesimal degrees.

Preferably, the plurality of inclination angles (of the rays emitted by the third illuminator) corresponds to a plurality of angles (to the viewing axis) distributed (preferably, but not necessarily, uniformly) in the entire interval [0; 90] sexagesimal degrees.

In one example embodiment, the plurality of inclinations (of the rays emitted from the third illuminator) corresponds to a plurality of angles (relative to the axis of vision) comprising at least a first, a second and a third angle, different and distinct one from the other. In one example, the first angle is the grazing light angle; said second angle is the top-down light angle; the third angle is intermediate between the first and the second angle (is greater than the second angle and less than the first angle).

In an embodiment, the third illuminator has at least three illuminating elements positioned at three different inclinations: a first inclination (first angle), which is substantially the same inclination of the illuminating elements of the first illuminator, a second inclination (second angle), which it is substantially the same inclination of the illuminating elements of the second illuminator, and at least a third inclination (at least said third angle), which is intermediate between said first and second inclination. In one example, the third illuminator has a plurality of illuminating elements positioned at a plurality of different inclinations, each of which inclinations is intermediate between said first and second inclination.

The inspection apparatus also comprises a processor connected to the camera and programmed to process the images captured by the camera.

The processor is programmed to generate, from each image captured, a first, a second and a third filtered image.

The first filtered image corresponds to the illumination contribution of the first illuminator considered individually. In other words, the first filtered image is equivalent to the image that the camera would have captured if only the first illuminator had been on (and the second and third illuminators off) during capture.

Similarly, the second filtered image corresponds to the illumination contribution of the second illuminator considered individually. In other words, the second filtered image is equivalent to the image that the camera would have captured if only the second illuminator had been on (and the first and third illuminators off) during capture.

Similarly, the third filtered image corresponds to the illumination contribution of the third illuminator considered individually. In other words, the third filtered image is equivalent to the image that the camera would have captured if only the third illuminator had been on (and the first and second illuminators off) during capture.

The fact that the apparatus, while capturing the image of the object, illuminates the object with a distributed light beam (meaning by that distributed over all the inclination angles, from the grazing light to the top-down light, inclusive) in addition to the beams oriented according to specific inclination angles (grazing and top-down) makes it possible to identify and distinguish very precisely the different types of defects typical of metal lids, making the apparatus particularly effective and reliable in checking the quality of the objects (in particular, metal lids).

The possibility, by data processing, of uncoupling the image contributions of the light beams generated by the different illuminators makes the apparatus particularly rapid, allowing a single image to be captured for each object without the risk of losing information.

Preferably, the first, second and third illuminators each have a corresponding plurality of illuminating elements (for example LEDs or incandescent lamps or other lighting bodies).

Preferably, the inspection apparatus comprises a beam splitter mirror interposed between the camera and the inspection station.

Preferably, the second illuminator has at least one illuminating element positioned upstream of the beam splitter mirror.

Preferably, the third illuminator has at least one illuminating element positioned upstream of the beam splitter mirror.

Thus, positioned upstream of the beam splitter mirror there are preferably at least one illuminating element of the second illuminator and at least one illuminating element of the third illuminator.

This makes the apparatus at once particularly effective in illuminating objects of different kinds and constructionally simple.

The processor is preferably programmed to process each of the first, second and third filtered images. This is useful because some types of defects are typically visible only on one of the filtered images. In other words, some defects are not visible on one or more of the filtered images and might not be visible or recognizable on the captured image (unfiltered).

Preferably, the processor is programmed to derive, for each of the first, second and third filtered images, a position of one or more defects identified on the filtered image itself.

The processor is also programmed to compare the first, second and third filtered images with each other.

More specifically, the processor is also programmed to check whether at a position corresponding to a defect found on one filtered image (for example, the first filtered image) there is a corresponding defect also on at least one of the other filtered images (the second or the third filtered image).

Thus, the processor is programmed to provide, for each defect detected on one of the filtered images and located at one position of the image, an indication of whether or not defects on the other filtered images have been detected at the same image position.

This is useful because to be able to reliably and precisely identify some types of defects, it is necessary not only to find that such defects are visible on one filtered image (for example, the image relating to grazing light only) but also to check whether or not that same defect is visible on other filtered images (for example, the image relating only to diffused light or light from above).

These features therefore allow setting a particularly effective defect diagnostic strategy (especially in the case of metal lids).

This description also provides a method for optical inspection of objects, in particular metal lids.

The method comprises a step of feeding the objects, preferably one by one, into an inspection station.

Once the object is inside the inspection station, a camera captures an image of the object below it (vertically aligned therewith along the viewing axis).

During capture, a lighting system illuminates the object positioned in the inspection station with three type of lighting. For this purpose, the lighting system comprises three illuminators: a first, a second and a third illuminator.

The first illuminator subjects the object to grazing light, with beams (or rays) of light at a first frequency.

The second illuminator subjects the object to light from above, with beams (or rays) of light at a second frequency.

The third illuminator subjects the object to diffused light, with beams (or rays) of light at a third frequency. To obtain the diffused light, the beams or rays of light at the third frequency are generated (simultaneously) at a plurality of different inclination angles to the viewing axis.

After the image has been captured, a digital representation of the image is generated and subjected to a processing step.

During the processing step, a first, a second and a third filtered image are derived from the captured image, each of which isolates the illumination contribution of a corresponding illuminator.

Preferably, for each of the first, second and third filtered images, processing also comprises identifying possible defects, for example by detecting dark zones on the image.

Processing also comprises, for each defect detected, storing the position of the defect on the image.

Preferably, processing also comprises comparing the first, second and third filtered images with each other.

For example, comparison comprises checking whether at a position on the image corresponding to a defect found on the first, second or third filtered image there is a corresponding defect also on at least one of the other filtered images, that is, the first, the second or the third filtered image.

The method also preferably comprises a step of identifying the type of defect by processing the information obtained from the above mentioned step of processing and comparing the filtered images. Identification is accomplished, for example, by an inference engine, for example a fuzzy inference engine.

BRIEF DESCRIPTION OF DRAWINGS

This and other features of the disclosure will become more apparent from the following detailed description of a preferred, non-limiting example embodiment of it, with reference to the accompanying drawings, in which.

DETAILED DESCRIPTION OF PREFERRED EMBODIMENTS OF THE INVENTION

Figure 1:
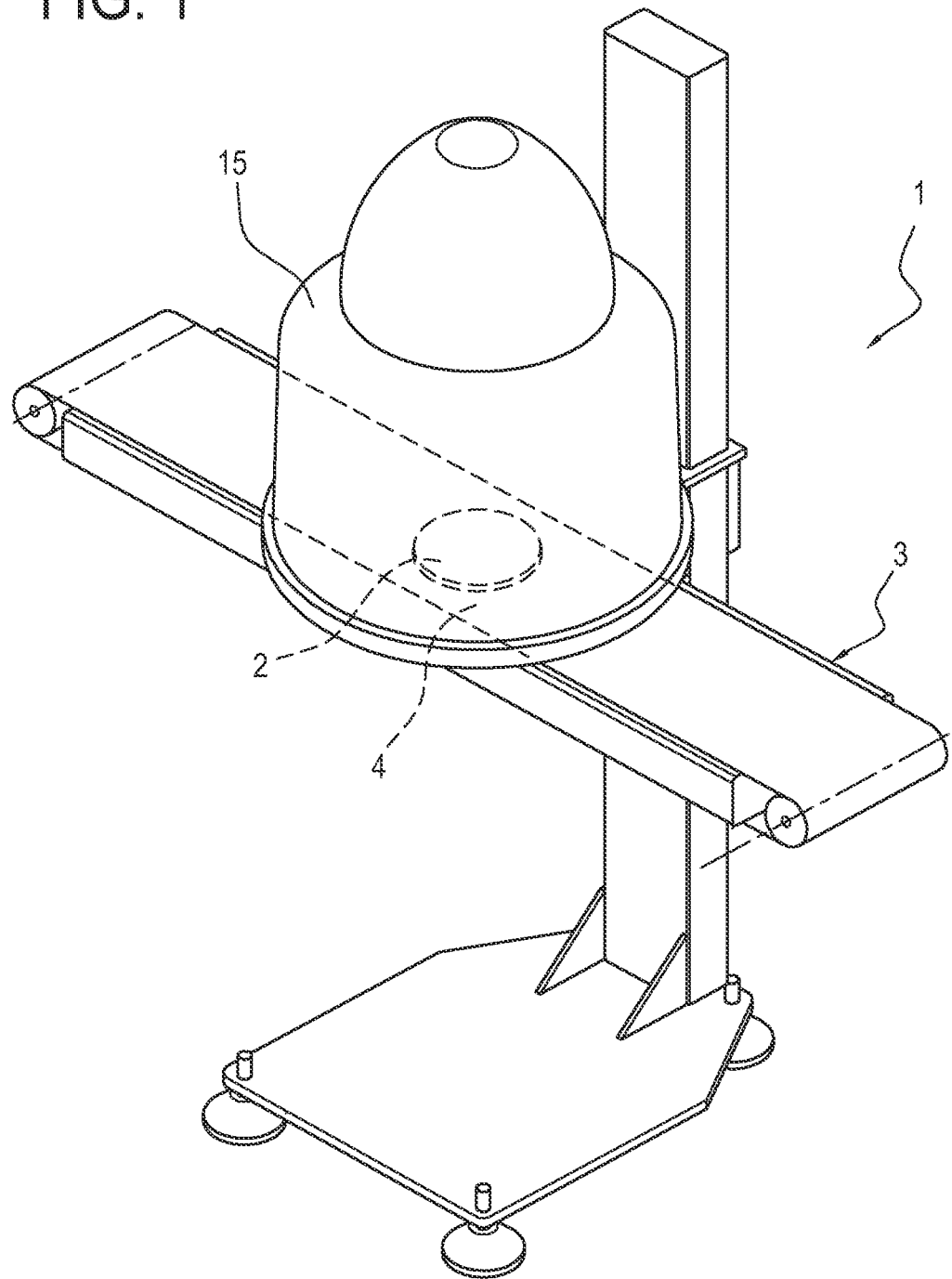
FIG. 1 shows a perspective view of an apparatus for optical inspection of objects according to this description.
Figure 2:
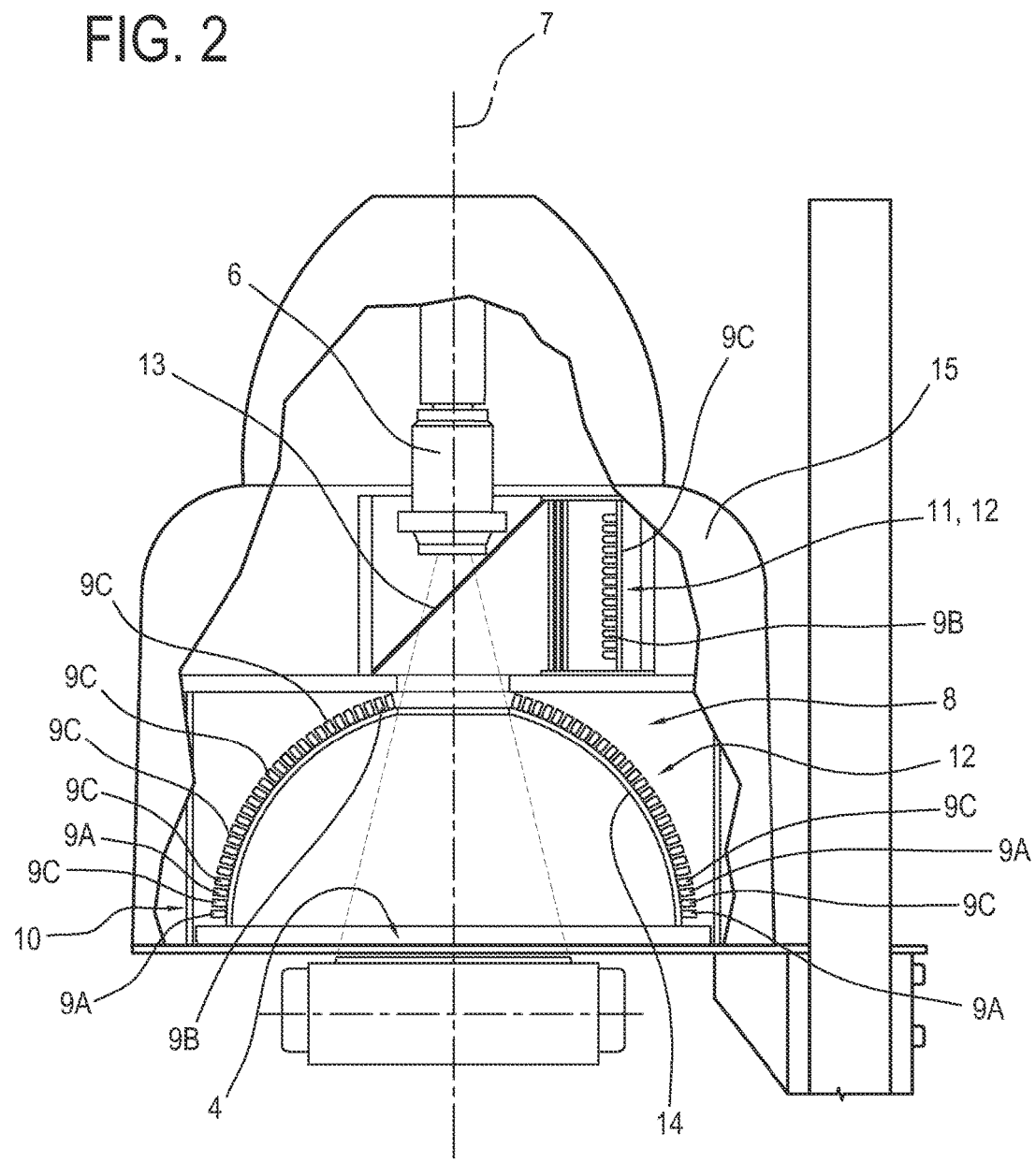
FIG. 2 illustrates a portion of the apparatus of FIG. 1 in a partly open side view
Figure 3:
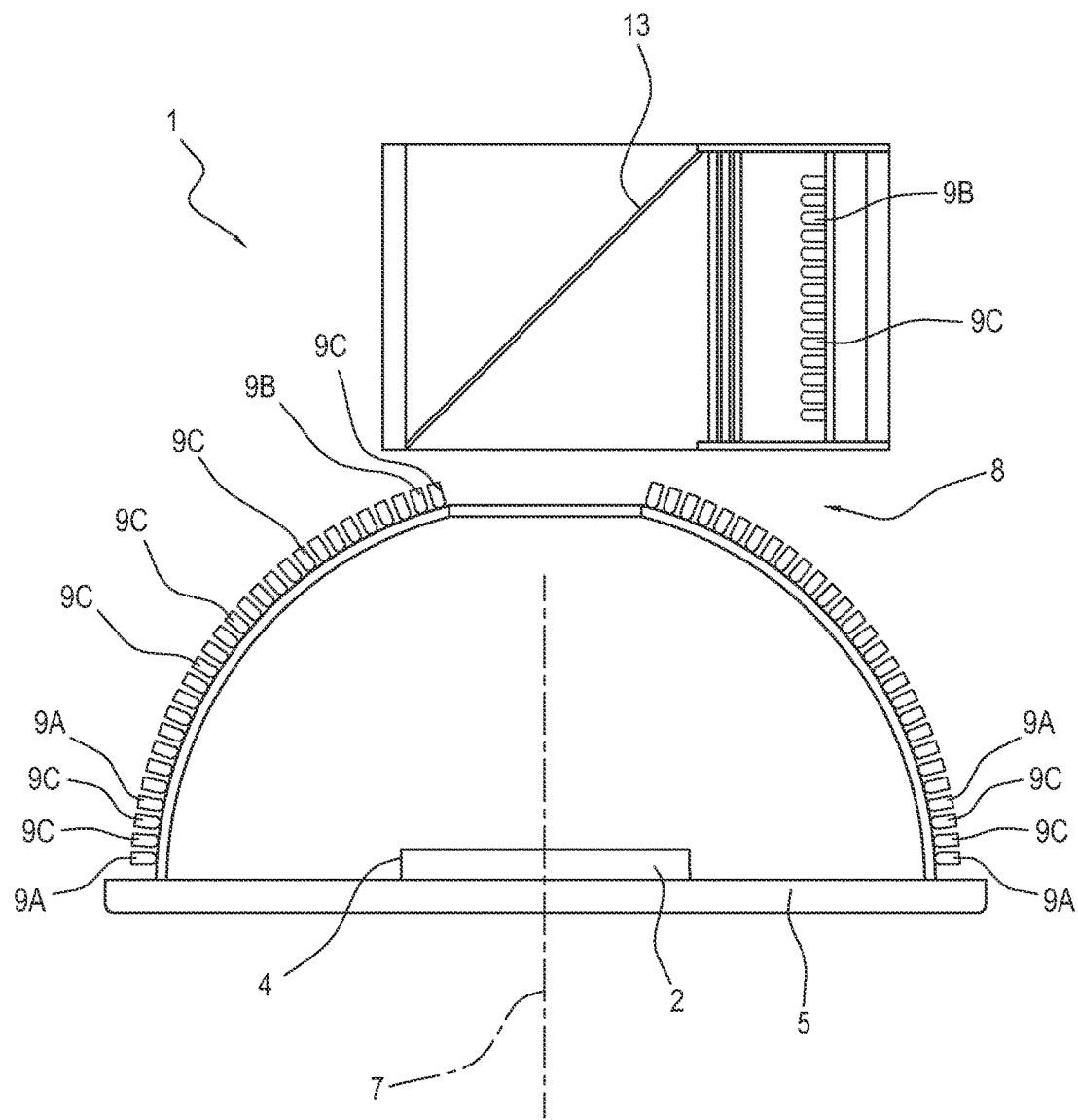
FIG. 3 illustrates a portion of the apparatus of FIG. 2 with an object present in the inspection station.

In the drawings, the numeral 1 denotes an apparatus for optical inspection of objects 2. More specifically, the objects 2 are made of metal. More specifically, the objects 2 are disc-shaped. More specifically, the objects 2 are metal lids.

The apparatus 1 comprises a conveyor 3 configured to feed the objects 2 towards and away from an inspection station 4.

In the example illustrated, the conveyor 3 is configured to feed the objects in a movement plane. In this example, the conveyor 3 is a belt.

The inspection station 4 defines a flat supporting surface 5 for the objects 2. In the example illustrated, the flat supporting surface 5 is a portion of the conveyor 3 located in the inspection station 4 from time to time.

The apparatus 1 comprises a camera 6 mounted above the flat supporting surface 5, in the inspection station 4, to see an object 2 below, positioned in the inspection station 4 itself.

The camera 6 is oriented according to a viewing axis 7 and is directed towards the flat supporting surface 5.

Preferably, the viewing axis is perpendicular to the flat supporting surface 5 of the objects 2 in the inspection station 4.

The apparatus 1 comprises a lighting system 8 to illuminate the object positioned in the inspection station 4 and allow the camera to capture an image of the object 2. The lighting system 8 comprises, preferably, a plurality of illuminating elements 9 (for example, LEDs).

The apparatus 1 (or the lighting system 8) comprises a first illuminator 10 configured to emit rays of light at a first frequency. For example, the first frequency is in the red (or infrared, or blue) spectrum.

In the example illustrated, the first illuminator 10 comprises a corresponding plurality of illuminating elements 9A. The plurality of illuminating elements 9A forming the first illuminator 10 constitutes a subset of the plurality of illuminating elements 9 of the lighting system 8.

The illuminating elements 9A of the first illuminator 10 are inclined at a first inclination angle to the viewing axis 7.

Preferably, the first inclination angle is such as to subject the object 2 in the inspection station 4 to grazing light. For example, the inclination angle is in the interval [80; 90] sexagesimal degrees.

The apparatus 1 (or the lighting system 8) comprises a second illuminator 11 configured to emit rays of light at a second frequency. For example, the second frequency is in the blue (or red, or ultraviolet) spectrum.

In the example illustrated, the second illuminator 11 comprises a corresponding plurality of illuminating elements 9B. The plurality of illuminating elements 9B forming the second illuminator 11 constitutes a subset of the plurality of illuminating elements 9 of the lighting system 8.

The illuminating elements 9B of the second illuminator 11 are inclined at a second inclination angle to the viewing axis 7.

Preferably, the second inclination angle is such as to subject the object 2 in the inspection station 4 to top-down light (light from above). For example, the inclination angle is in the interval [0; 20] sexagesimal degrees.

The apparatus 1 (or the lighting system 8) comprises a third illuminator 12 configured to emit rays of light at a third frequency. For example, the third frequency is in the green (or red or blue) spectrum.

In the example illustrated, the third illuminator 12 comprises a corresponding plurality of illuminating elements 9C. The plurality of illuminating elements 9C forming the third illuminator 12 constitutes a subset of the plurality of illuminating elements 9 of the lighting system 8.

The illuminating elements 9C of the third illuminator 12 are inclined at a plurality of different inclination angles to the viewing axis 7, included between 0 and 90 sexagesimal degrees. Thus, the third illuminator 12 is configured to illuminate the object 2 with diffused light at the third frequency.

More specifically, the third illuminator 12 is mounted on a three-dimensional surface which surrounds the inspection station 4 in a half-space defined by the flat supporting surface 5 and containing the camera 6. More specifically, the three-dimensional surface surrounds and extends around the optical path defined by the camera 6.

The apparatus 1 also comprises a processor (not illustrated in the drawings), that is, a data processing unit. The processor may be part of a computer, or it may be embodied by a suitably programmed CPU, or an electronic card or other known solutions for embodying data processing means.

The processor is connected to the camera 6 and is programmed to process the images captured by the camera 6 itself.

More specifically, from each image captured by the camera, the processor is programmed to generate a first, a second and a third filtered image.

The first, second and third filtered images each correspond to the illumination contribution of the first, second or third illuminator 10, 11, 12, respectively and separately (that is, isolated from the other image contributions of the other illuminators). Preferably, the three-dimensional surface is bell- or dome-shaped. In other embodiments, it is cylindrical, hemispherical or conical.

In one example embodiment, the apparatus 1 comprises a beam splitter mirror 13 interposed between the camera 6 and the inspection station 4.

Preferably, one or more of the illuminating elements 9C of the third illuminator 12 are positioned upstream of the beam splitter mirror 13.

Alternatively or, preferably, in addition, one or more of the illuminating elements 9B of the second illuminator 11 are positioned upstream of the beam splitter mirror 13.

Preferably, the illuminating elements 9A of the first illuminator 10 (or a subset thereof) are arranged in a ring around the viewing axis 7. The illuminating elements 9A of the first illuminator 10 arranged in a ring are located at a position proximal to the inspection station 4 (that is, to the flat supporting surface 5 on which the object 2 photographed by the camera 6 is resting).

Preferably, the illuminating elements 9B of the second illuminator 11 (or a subset thereof) are arranged in a ring around the viewing axis 7.

The illuminating elements 9B of the second illuminator 11 arranged in a ring are located at a position distal from the inspection station 4 (that is, from the flat supporting surface 5 on which the object 2 photographed by the camera 6 is resting).

Preferably, at least one subset of the illuminating elements 9C of the third illuminator 12 are distributed on the three-dimensional surface.

In one example embodiment, the apparatus 1 also comprises a diffuser 14 interposed between the illuminators 10, 11 and 12 (that is, the illuminating elements 9) and the inspection station 4.

The diffuser 14 is a body defining a concave surface positioned around the viewing axis 7. Preferably, the diffuser 14 has the shape of a bell, or a dome, or a cylinder, or a cone.

In one example embodiment, the illuminators 10, 11 and 12 and the camera 6 (and the diffuser 14, if present) are contained in a shell 15, that is to say, they are surrounded by the shell 15.

Preferably, the processor is programmed to derive, for each of the first, second and third filtered images, a position of one or more defects identified on the filtered image. The processor is also programmed to compare the first, second and third filtered images with each other in order to check whether at a position on the image corresponding to a defect found on the first, second or third filtered image there is a corresponding defect also on at least one of the other filtered images, that is, the first, the second or the third filtered image.

Operatively, the apparatus 1 according to this description works as follows.

A conveyor 3 feeds a succession of objects 2 (individually) to the inspection station 4.

Preferably, the apparatus detects the presence of the object 2 in the inspection station 4 and drives the camera 6 to capture the image (preferably a single image).

In an example embodiment, the conveyor 3 stops for a certain interval of time when the object 2 is in the inspection station 4, and then moves intermittently. In another embodiment, the conveyor does not stop during capture operations.

During capture of the image of the object 2, the object 2 is illuminated simultaneously with different types of light, which differ in the angle of the illuminating light rays incident upon the object 2 illuminated (this angle being referenced in this description to the viewing axis 7 of the camera 6, without in any way limiting the scope of the description).

The rays or beams of light belonging to different types of light differ in frequency (in the frequency spectrum of the light which illuminates the object 2).

Preferably, during image capture, the object 2 is illuminated simultaneously with grazing light (at a first frequency); with top-down light (at a second frequency) and with diffused light (at a third frequency).

The image captured is processed to generate (that is, derive) two or more filtered images, each of which isolates the illumination contribution of a single type of light.

For example, the image captured is processed to derive a first, a second and a third filtered image corresponding to the contributions of the grazing light, of the top-down light and of the diffused light, respectively (and separately).

Preferably, processing comprises comparing the filtered images with each other to obtain indications as to whether or not a defect visible with one type of light is also visible with another type of light.

Preferably, for each first, second and third filtered image, the processing step comprises, in the event of defects being detected, deriving (and storing) data regarding the position of the defects on the image. Also, preferably, processing comprises verifying whether a corresponding defect is present or absent (that is, visible or invisible) at the same (that is, corresponding) position on the other filtered images. Lighting may be continuous or stroboscopic.

The invention claimed is:

1. An apparatus for optical inspection of objects, in particular metal lids, comprising:
 a camera oriented according to a vertical viewing axis to see the object to be inspected positioned in an inspection station and to capture an image of the object;
 a first illuminator configured to emit rays of light at a first frequency, and being inclined at a first inclination angle to the viewing axis to subject the object in the inspection station to grazing light at the first frequency;
a second illuminator configured to emit rays of light at a second frequency different from the first frequency, and being inclined at a second inclination angle to the viewing axis, smaller than the first inclination angle, to subject the object in the inspection station to top-down light at the second frequency;
a third illuminator configured to emit rays of light at a third frequency, different from the first and second frequencies;
a processor connected to the camera and programmed to process the captured image and generate from it a first, a second and a third filtered image corresponding to the illumination contributions of the first, second and third illuminators, respectively and separately,
wherein the third illuminator is mounted on a three-dimensional surface positioned around the inspection station and around an optical path defined by the camera, so that the light rays emitted by the third illuminator are inclined at a plurality of different inclination angles to subject the object in the inspection station to diffused light at the third frequency,
the third illuminator including a plurality of lighting elements, wherein:
  a first lighting element of the plurality of lighting elements of the third illuminator is inclined, with respect to the viewing axis, according to a third inclination angle, the third inclination angle being smaller than the first inclination angle of the first illuminator;
  a second lighting element of the plurality of lighting elements of the third illuminator is inclined, with respect to the viewing axis, according to the second inclination angle of the second illuminator;
whereby both the second illuminator and the second lighting element of the plurality of lighting elements of the third illuminator are inclined at the second inclination angle, to subject the object in the inspection station to top-down light.

2. The apparatus according to claim 1, wherein the third frequency is in the green spectrum.

3. The apparatus according to claim 1, wherein the first frequency is in the red spectrum and the second frequency is in the blue spectrum.

4. The apparatus according to claim 1, wherein the three-dimensional surface has the shape of a bell or a dome.

5. The apparatus according to claim 1, comprising a beam splitter mirror interposed between the camera and the inspection station, wherein the second and third illuminators each have a corresponding plurality of illuminating elements, wherein at least one of the illuminating elements of the second illuminator and at least one of the illuminating elements of the third illuminator are positioned upstream of the beam splitter mirror.

6. The apparatus according to claim 1, wherein the first, second and third illuminators each have a corresponding plurality of illuminating elements, wherein:
  the illuminating elements of the first illuminator are arranged in a ring at a proximal position relative to the inspection station;
  the plurality of illuminating elements of the second illuminator has a group of illuminating elements arranged in a ring at a distal position relative to the inspection station;
  the plurality of illuminating elements of the third illuminator has a group of illuminating elements positioned on the three-dimensional surface.

7. The apparatus according to claim 1, comprising a diffuser interposed between the illuminators and the inspection station, positioned around the viewing axis and having the shape of a bell or a cylinder.

8. The apparatus according to claim 1, wherein the processor is programmed to derive from each of the first, second and third filtered images, a position of one or more defects detected on the filtered image and is also programmed to compare the first, second and third filtered images with each other to check if, at a position on the image corresponding to a defect detected on one of the first, second or third filtered image, there is also a corresponding defect also on at least one of the other filtered images of the first, second or third filtered image.

9. The apparatus according to claim 1, comprising a conveyor configured to feed the objects towards and away from the inspection station along a movement plane perpendicular to the viewing axis.

10. The apparatus according to claim 1, wherein the third illuminator has a plurality of lighting elements oriented in at least three different orientations, including a first, a second and a third angle, wherein the first and the second angle correspond to said first and second inclination angle of the first and second illuminator, respectively, and the third angle is smaller than the first inclination angle and larger than the second inclination angle.

11. Apparatus according to claim 1, wherein the third illuminator includes a plurality of lighting elements, wherein:
  a group of third lighting elements of the plurality of lighting elements of the third illuminator is oriented, with respect to the viewing axis, according to respective different angles, said angles being smaller than the third inclination angle and larger than the second inclination angle.

12. A method for optically inspecting objects, in particular metal lids, comprising the following steps:
  feeding the objects individually into an inspection station;
  capturing an image of the object positioned in the inspection station through a camera mounted above the object and oriented according to a vertical viewing axis;
  during capture, illuminating the object with grazing light at a first frequency, illuminating the object with top-down light at a second frequency and illuminating the object with light at a third frequency, wherein the first, second and third frequencies are different from each other;
  processing the captured image and generating a first, a second and a third filtered image corresponding to the illumination contributions of the first, second and third illuminators, respectively and separately,
wherein, during capture, the light at the third frequency is diffused by means of rays inclined at a plurality of different, distributed inclination angles from the condition of grazing light to that of top-down light,
wherein the light at the third frequency is diffused by means of rays inclined, with respect to the viewing axis, a third inclination angle, the third inclination angle being smaller than the first inclination angle of the first illuminator and at the second inclination angle of the second illuminator,
whereby both the second illuminator and the second lighting element of the plurality of lighting elements of the third illuminator are inclined at the second inclination angle, to subject the object in the inspection station to top-down light.

13. The method according to claim 12, wherein processing comprises:

for each first, second and third filtered image, detecting defects, if any, and deriving the positions of the defects on the image;

comparing the first, second and third filtered images with each other in order to check whether at a position on the image corresponding to a defect found on the first, second or third filtered image there is a corresponding defect also on at least one of the other filtered images, that is, on the first, the second or the third filtered image.

14. The method according to claim 12, wherein in feeding the objects, the objects are moved along a movement plane perpendicular to the viewing axis and wherein the camera takes a single image of each object.

15. The method according to claim 12, wherein the illumination at the third frequency provides to subject the object, simultaneously, to grazing lighting, top-down lighting and lighting according to one or more inclinations intermediate with respect to the inclinations corresponding to grazing and top lighting.

16. The apparatus according to claim 11, wherein said different inclination angles of the group of lighting elements of the plurality of lighting elements of the third illuminator are uniformly distributed all over an inclination range defined between the first inclination angle and the third inclination angle.

17. Apparatus according to claim 1, wherein the three-dimensional surface is dome-shaped.

18. Apparatus according to claim 1, wherein the three-dimensional surface has a conical shape.

* * * * *